US009933392B2

United States Patent
Kollgaard (10) Patent No.: US 9,933,392 B2
(45) Date of Patent: Apr. 3, 2018

(54) APPARATUS, SYSTEM, AND METHOD FOR NON-DESTRUCTIVE ULTRASONIC INSPECTION

(71) Applicant: The Boeing Company, Chicago, IL (US)

(72) Inventor: Jeffrey R. Kollgaard, Seattle, WA (US)

(73) Assignee: The Boeing Company, Chicago, IL (US)

( * ) Notice: Subject to any disclaimer, the term of this patent is extended or adjusted under 35 U.S.C. 154(b) by 254 days.

(21) Appl. No.: 14/871,588

(22) Filed: Sep. 30, 2015

(65) Prior Publication Data

US 2017/0089866 A1  Mar. 30, 2017

(51) Int. Cl.
*G01N 29/22* (2006.01)
*G01N 29/04* (2006.01)

(52) U.S. Cl.
CPC ......... *G01N 29/043* (2013.01); *G01N 29/225* (2013.01); *G01N 2291/0231* (2013.01); *G01N 2291/048* (2013.01); *G01N 2291/102* (2013.01)

(58) Field of Classification Search
CPC .............. G01N 29/043; G01N 29/225; G01N 2291/102; G01N 2291/048; G01N 2291/0231
USPC .......................................................... 73/587
See application file for complete search history.

(56) References Cited

U.S. PATENT DOCUMENTS

| | | | | |
|---|---|---|---|---|
| 3,850,028 A | * | 11/1974 | Thompson | G01N 29/2412 324/226 |
| 5,363,078 A | * | 11/1994 | Ries | H01F 7/0278 324/319 |
| 5,665,893 A | * | 9/1997 | Smith | G01H 3/005 73/1.82 |
| 5,935,346 A | * | 8/1999 | Couderchon | C21D 1/04 148/108 |
| 6,722,202 B1 | | 4/2004 | Kennedy et al. | |
| 6,927,560 B2 | | 8/2005 | Pedigo et al. | |
| 7,231,826 B2 | | 6/2007 | Bossi et al. | |
| 7,240,556 B2 | | 7/2007 | Georgeson et al. | |
| 7,313,959 B2 | | 1/2008 | Georgeson et al. | |
| 7,498,796 B2 | | 3/2009 | Georgeson et al. | |

(Continued)

FOREIGN PATENT DOCUMENTS

WO    WO2005038391    *  4/2005

*Primary Examiner* — J M Saint Surin
(74) *Attorney, Agent, or Firm* — Kunzler, PC (57) ABSTRACT

An apparatus, for non-destructively inspecting a sandwich panel defining an enclosed space, has an external and internal probe. The external probe is adjacent an external face-sheet of the sandwich panel and the internal probe is adjacent an internal face-sheet of the sandwich panel. The sandwich panel has a core material that is is interposed between the external and internal face-sheets of the sandwich panel. Each of the probes includes two elements that integrally form the probe. The external probe includes and is integrally formed from one of a magnetic field emitter and a magnetic field sensor, the magnetic field emitter emitting a magnetic field, and one of an ultrasonic transmit transducer and an ultrasonic receive transducer. The internal probe includes and is integrally formed from the other of the magnetic field emitter and the magnetic field sensor and the other of the ultrasonic transmit transducer and the ultrasonic receive transducer.

20 Claims, 5 Drawing Sheets

(56) References Cited

U.S. PATENT DOCUMENTS

| | | |
|---|---|---|
| 7,768,249 B2 | 8/2010 | Georgeson et al. |
| 7,768,250 B2 | 8/2010 | Georgeson et al. |
| 8,749,230 B1 | 6/2014 | Fogarty et al. |
| 2009/0301206 A1* | 12/2009 | Yashan .................. G01N 27/87 73/643 |

* cited by examiner

APPARATUS, SYSTEM, AND METHOD FOR NON-DESTRUCTIVE ULTRASONIC INSPECTION

FIELD

This disclosure relates generally to ultrasonic inspection, and more particularly relates to non-destructive ultrasonic inspection of sandwich panels.

BACKGROUND

Load-bearing structures, such as airframe components and structural assemblies, must be properly manufactured and maintained in order to prevent structural defects such as cracking, corrosion, delamination, and the like. Accordingly, damage inspection on such structures is important in order to detect and repair flaws, thus preventing the occurrence of these negative consequences.

Some structures, such as panels that define an enclosed space, are particularly difficult to inspect for structural defects. For example, sandwich panels that define an enclosed space are often difficult to inspect because most conventional inspection techniques are configured to examine and detect the external skin and are thus unable to adequately inspect the core and internal skin of the sandwich panel. Further, access to an enclosed space defined by a sandwich panel is often limited, thus making it difficult to properly position inspection devices adjacent interior surfaces within an enclosed space.

SUMMARY

The subject matter of the present application has been developed in response to the present state of the art, and in particular, in response to the problems associated with, and the need to, detect structural damage, such as crack formations, and abnormalities, in sandwich panels that define an enclosed space. Accordingly, the subject matter of the present application has been developed to provide an apparatus, system, and method for inspecting sandwich panels defining an enclosed space that overcome at least some of the above-discussed shortcomings of prior art techniques.

Disclosed herein is one embodiment of an apparatus for non-destructively inspecting a sandwich panel defining an enclosed space. The apparatus includes an external probe and an internal probe. The external probe is adjacent an external face-sheet of the sandwich panel and the internal probe is adjacent an internal face-sheet of the sandwich panel. The sandwich panel has a core material interposed between the external and internal face-sheets. Each of the probes includes two elements that integrally form the probe. The external probe includes and is integrally formed from one of a magnetic field emitter and a magnetic field sensor, the magnetic field emitter emitting a magnetic field, and one of an ultrasonic transmit transducer and an ultrasonic receive transducer. The internal probe includes and is integrally formed from the other of the magnetic field emitter and the magnetic field sensor and the other of the ultrasonic transmit transducer and the ultrasonic receive transducer.

According to one implementation, non-destructive access to the enclosed space is limited to an access hole having a diameter less than three inches. In such an implementation, the internal probe may have a cross-sectional dimension that is less than the diameter of the access hole such that the internal probe is passable through the access hole. For example, the internal probe may be affixed to an extension arm, wherein the extension arm is positionable to extend from the access hole to allow a user to grasp a portion of the extension arm external the enclosed space and control the position of the internal probe within the enclosed space.

In one implementation, the sandwich panel has a honeycomb core material disposed between the external face-sheet and the internal face-sheet. According to another implementation, the external probe has the magnetic field sensor and the ultrasonic transmit transducer. The magnetic field sensor may be an eddy current sensor coil that is wrapped around and concentric with the ultrasonic transmit transducer. In such an implementation, the internal probe includes the magnetic field emitter and the ultrasonic receive transducer. The magnetic field emitter may be multiple magnetic material components circumferentially positioned around and collectively concentric with the ultrasonic receive transducer. According to another implementation, the magnetic field emitter is a material having a high magnetic permeability, such as ferrite, and the magnetic field sensor is an eddy current sensor coil. In some implementations, the magnetic field emitter is a material having a relative magnetic permeability between about 16 and about 5,000.

Also disclosed herein is one embodiment of a method for non-destructively inspecting a sandwich panel defining an enclosed space. In one implementation, non-destructive access to the enclosed space is limited to an access hole. The method includes inserting an internal probe through the access hole. The internal probe may be affixed to an extension arm and at least a portion of the extension arm may remain external the enclosed space. The method further includes moving an external probe external the enclosed space to a desired inspection position on an external face-sheet of the sandwich panel. After moving the external probe to the desired inspection position, the method includes moving the internal probe across an internal face-sheet of the sandwich panel to determine an alignment position where a maximum magnetic field strength of a magnetic field emanating from a magnetic field emitter of one of the internal and external probe is detected by a magnetic field sensor of the other of the internal and external probe. With the external probe at the desired inspection position and the internal probe at the alignment position, the method includes detecting an ultrasonic signal from an ultrasonic transmit transducer of one of the internal and external probe by an ultrasonic receive transducer of the other of the internal and external probe.

According to one implementation, the method includes applying a couplant gel to the internal face-sheet of the sandwich panel using an extendable paintbrush or other suitable applicator before inserting the internal probe through the access hole. In such an implementation, moving the internal probe across the internal face-sheet of the sandwich panel comprises moving the ultrasonic receive transducer across the internal face-sheet of the sandwich panel in contact with the couplant gel. In another implementation, the method further includes applying a couplant gel to the external face-sheet of the sandwich panel before moving the external probe to the desired inspection point and contacting the ultrasonic transmit transducer of the external probe to the external face-sheet of the sandwich panel via couplant gel.

In another implementation, the method further includes determining the presence of structural anomalies by comparing the ultrasonic signal with an expected ultrasonic reading. For example, a structural anomaly may be detected if the difference between the ultrasonic signal and the expected ultrasonic reading is more than 18 decibels. In one implementation, moving the external probe is automated by a robotic device controlled by a controller. In another implementation, moving the internal probe is automated by a robotic device controlled by a controller.

In one implementation, detecting the ultrasonic signal from the ultrasonic transmit transducer by the ultrasonic receive transducer includes continually transmitting and receiving ultrasounds but only recording the ultrasonic signal when the external probe is at the desired inspection position and the internal probe is at the alignment position. In yet another implementation, detecting the ultrasonic signal from the ultrasonic transmit transducer by the ultrasonic receive transducer comprises transmitting and receiving ultrasounds only when the external probe is at the desired inspection position and the internal probe is at the alignment position.

Also disclosed herein is one embodiment of an inspection system for non-destructively inspecting a sandwich panel defining an enclosed space. The system includes an external probe and an internal probe. The external probe is adjacent an external face-sheet of the sandwich panel and the internal probe is adjacent an internal face-sheet of the sandwich panel. The sandwich panel includes a core material interposed between the external and internal face-sheets. Each of the probes includes two elements that integrally form the probe. The external probe includes and is integrally formed from one of a magnetic field emitter and a magnetic field sensor, the magnetic field emitter emitting a magnetic field, and one of an ultrasonic transmit transducer and an ultrasonic receive transducer. The internal probe includes and is integrally formed from the other of the magnetic field emitter and the magnetic field sensor and the other of the ultrasonic transmit transducer and the ultrasonic receive transducer. The system further includes a controller. The controller includes a movement module, an alignment module, and a data module. The movement module is configured to move one of the external probe and the internal probe to an inspection position. The alignment module is configured to move the other of the external probe and the internal probe to an alignment position. The data module is configured to detect an ultrasonic signal from the ultrasonic transmit transducer by the ultrasonic receive transducer when the one of the external probe and the internal probe is in the inspection position and when the other of the external probe and the internal probe is in the alignment position.

In one implementation, the data module is further configured to determine the presence of structural anomalies by comparing the ultrasonic signal with an expected ultrasonic reading. In another implementation, a structural anomaly is detected if the difference between the ultrasonic signal and the expected ultrasonic reading is more than 18 decibels.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter, they are not therefore to be considered to be limiting of its scope. The subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

As described above, the apparatus, system, and method disclosed herein are related to the non-destructive, through-transmission, ultrasonic inspection of sandwich panels 70 that define an enclosed space 75. In other words, the apparatus 100 of the present disclosure is configured to inspect the structural integrity of sandwich panels 70, which are comparatively thicker than laminate panels and have a core material 73 that is not easily inspected by using conventional inspection techniques. The sandwich panel 70 includes an external face-sheet 71 and an internal face-sheet 72 ("external" and "internal" relative to the enclosed space 75), with the core material 73 being interposed between the two face-sheets 71, 72. The process of inspecting the sandwich panel 70 is non-destructive, thus allowing, for example, an airplane manufacturer or an airplane servicer to inspect the sandwich panel 70 in situ without having to substantially disassemble or destroy the structure.

Figure 1A:
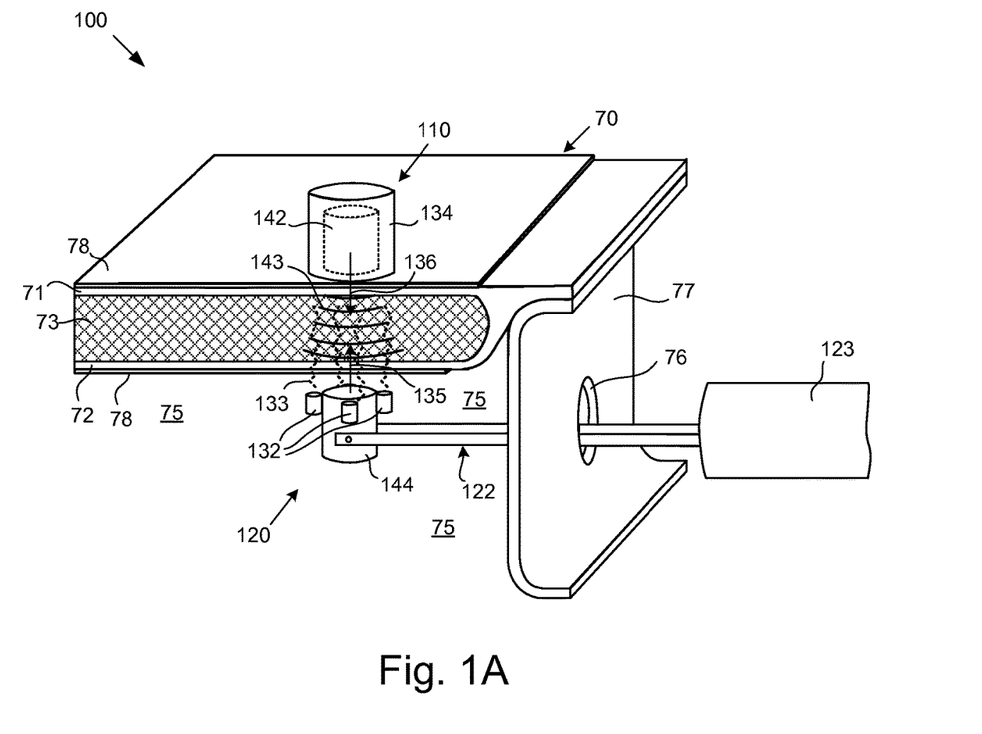
FIG. 1A is a schematic partial perspective view of an apparatus for inspecting a sandwich panel defining an enclosed space, according to one embodiment.

FIG. 1A is a schematic partial perspective view of the apparatus 100 for inspecting the sandwich panel 70 that defines an enclosed space 75, according to one embodiment. As depicted in FIG. 1A, only a portion (e.g., cross-section) of the sandwich panel 70 is shown in order to show the features of the apparatus 100 more clearly. Accordingly, although only a portion of the sandwich panel 70 is shown in FIG. 1A, it is recognized that in some embodiments, the sandwich panel 70, in cooperation with other components, such as the spar 77, additional sandwich panels, and the like, collectively define the enclosed space 75, which may only be accessible via an access hole 76. In other words, although the enclosed space 75 is not depicted in FIG. 1A as being fully enclosed, with some features defining the enclosed space 75 being only partially shown or removed in order to more clearly show the features of the apparatus 100, the enclosed spaced 75 is substantially completely enclosed but for the access hole 76.

The apparatus 100 includes an external probe 110 and an internal probe 120. The external probe 110 is configured to be positioned adjacent the external face-sheet 71 of the sandwich panel 70. The internal probe 120 is configured to be extended into the enclosed space 75 through the access hole 76 and positioned adjacent the internal face-sheet 72 of the sandwich panel 70. Each of the probes 110, 120 includes a magnetic element and an ultrasonic element both integrally coupled together to form the respective probe. In other words, the magnetic element and the ultrasonic element of each probe are permanently integrated together to form a unitary structure. Thus, the two elements of each probe 110, 120 are not merely functionally coupled together, but instead are integrally/physically connected together to form each of the probes 110, 120. In this manner, movement of a probe concurrently moves both the ultrasonic element and magnetic element of that probe.

The magnetic element of each probe includes one of a magnetic field emitter 132 and a magnetic field sensor 134. More specifically, the magnetic element of one probe includes one of the magnetic emitter 132 and the magnetic field sensor 134, and the magnetic element of the other probe includes the other of the magnetic emitter 132 and the magnetic field sensor 134. The magnetic field emitter 132 emits a magnetic field 133 and the magnetic field sensor 134 detects the magnetic field strength of the magnetic field 133. The ultrasonic element of each probe includes one of an ultrasonic transmit transducer 142 and an ultrasonic receive transducer 144. More specifically, the ultrasonic element of one probe includes one of the ultrasonic transmit transducer 142 and the ultrasonic receive transducer 144, and the ultrasonic element of the other probe includes the other of the ultrasonic transmit transducer 142 and the ultrasonic receive transducer 144. The ultrasonic transmit transducer 142 emits an ultrasonic signal 143 and the ultrasonic receive transducer 144 detects the presence, strength, and/or properties of the ultrasonic signal 143. Generally, the magnetic elements 132, 134 are used to align the probes 110, 120 so that the ultrasonic elements can also be aligned for accurate ultrasonic through-transmission inspection. Additional details relating to the probes 110, 120 and the magnetic and ultrasonic elements are included below.

In the depicted embodiment, the external probe 110 includes and is integrally formed with the magnetic field sensor 134 and the ultrasonic transmit transducer 142, and the internal probe 120 includes and is integrally formed with the magnetic field emitter 132 and the ultrasonic receive transducer 144. However, in another embodiment, the external probe 110 may include the magnetic field emitter 132 and the ultrasonic transmit transducer 142, and the internal probe 120 may include the magnetic field sensor 134 and the ultrasonic receive transducer 144, or vice-versa. Thus, the external probe 110 has one of either the magnetic field emitter 132 and the magnetic field sensor 134 and also one of either the ultrasonic transmit transducer 142 and the ultrasonic receive transducer 144, while the internal probe 120 has the other of either the magnetic field emitter 132 and the magnetic field sensor 134 and also the other of either the ultrasonic transmit transducer 142 and the ultrasonic receive transducer 144.

In one embodiment, the configuration of the probes 110, 120 is based on the physical dimensions of the individual magnetic and ultrasonic elements in view of the dimensions of the sandwich panel 70 and/or enclosed space 75 being inspected. For example, relatively stronger magnetic elements and/or stronger ultrasonic elements may be required for comparatively thicker sandwich panels 70 or for sandwich panels 70 having s specific core material 73 structure. Further, the relative size difference between the magnetic field emitter 132 and the magnetic field sensor 134 may be determinative of which one forms part of the internal probe 120. For example, if the access hole 76 has a relatively small diameter and/or the dimensions of the enclosed space 75 are such that there is little room within the enclosed space 75 to maneuver, the smaller of the magnetic elements may be integrated with the smaller of the ultrasonic elements to form the internal probe 120.

In the embodiment depicted, the magnetic field sensor 134 of the external probe 110 is an eddy current sensor coil that is wrapped around and concentric with the ultrasonic transmit transducer 142. Correspondingly, the internal probe 120 has a magnetic field emitter 132 that is made from multiple magnetic material components circumferentially positioned around and collectively concentric with the ultrasonic receive transducer 144. The magnetic field emitter 132 (e.g., the multiple magnetic material components) may be a static magnetic material, such as a permanent magnet, or the magnetic field emitter 132 may be active, such as an electromagnet. For example, an electromagnetic may be used so that the magnetic field strength can be varied according to the configuration (thickness, density, etc.) of the sandwich panel 70. Where strong magnetic fields 133 are not required or desired, the magnetic field emitter 132 may be made from a passive material, such as ferrite or other materials that have high magnetic permeability, that is detectable with eddy current sensors. Ferrite materials, for example, have a relative magnetic permeability between about 16 and about 640. Other materials suitable for forming the magnetic field emitter 132 may have a relative magnetic permeability between about 16 and about 5,000. Such high magnetic permeability materials produce a distorted magnetic field that is easily detected by eddy current sensors.

The ultrasonic elements, the ultrasonic transmit transducer 142 and the ultrasonic receive transducer 144, may be ultrasonic wave transducers that transmit ultrasonic waves through the sandwich panel and then receive the propagated ultrasonic waves, respectively. The ultrasonic transmit transducer 142 and the ultrasonic receive transducer 144 may be of the same type of ultrasonic transducer in some implementations. In one implementation, the ultrasonic transmit transducer 142 generates an ultrasonic wave with a frequency of about 1 MHz. The pulse characteristics (e.g., amplitude) of the ultrasonic signal 143 generated by the ultrasonic transmit transducer 142 may be compared to the pulse characteristics of the propagated ultrasonic signal 143 detected and received by the ultrasonic receive transducer 144 (after passing through the sandwich panel) to determine if defects exist in the structure. Further, the received ultrasonic signal 143 may be compared to an expected ultrasonic signal from a comparable sandwich panel that is free of structural defects.

The type of wave transducers utilized for a specific embodiment may be selected according to the type of structure that is being inspected. For example, certain wave transducers may be comparatively better-suited for metallic structures while other wave transducers may be comparatively better-suited for composite structures. Further, in certain implementations, a couplant gel 78 or a couplant liquid may be used to enhance the transmission of the ultrasonic signal 143 from the ultrasonic transmit transducer 142 into the sandwich panel 70 and also the transmission of the ultrasonic signal 143 from the sandwich panel 70 to the ultrasonic receive transducer 144. In other words, one or both of the face-sheets 71, 72 of the sandwich panel 70 may be coated with the couplant gel 78 before using the apparatus 100.

As described above, the access hole 76 may be a preformed aperture in one of the walls defining the enclosed space 75. In certain structures, the size of the access hole 76 is limited in order to ensure the structure has sufficient strength. Accordingly, in one embodiment the access hole 76 has a diameter that is less than 3 inches. In another embodiment the access hole 76 has a diameter that is less than 2 inches. In yet another embodiment, the access hole has a diameter that is about 1.5 inches. Accordingly, the internal probe 120 has a cross-sectional dimension that is less than the diameter of the access hole 76 such that the internal probe is passable through the access hole.

The apparatus 100 may also include an extension arm 122 attached to the internal probe 120. The extension arm 122 is positionable so that at least a portion 123 of the extension arm extends from the access hole 76 (e.g., is accessible outside the enclosed space 75) to allow a user to grasp, or enable a mechanical mechanism to be coupled to, the extension arm 122 to control the position of the internal probe 120 within the enclosed space 75. Accordingly, as described below in greater detail, the movement and positioning of the probes may be accomplished manually by a user grasping the probes 110, 120 or one or both of the probes 110, 120 may be coupled to a robotic arm that is controlled by a controller.

In one embodiment, the extension arm 122 is rotatably coupled to the internal probe 120, thus enabling the magnetic field emitter 132 and the ultrasonic receive transducer 144 to maintain a desired orientation relative to the internal face-sheet 72 of the sandwich panel 70 (a similar configuration may be implemented with the external probe 110). In other words, maintaining a proper orientation of the probes 110, 120 relative to the face-sheets 71, 72 of the sandwich panel 70 may be important in performing an accurate and reliable inspection. For example, the magnetic elements 132, 134 and the ultrasonic elements 142, 144 may be configured to have a signal axis. In other words, the magnetic field emitter 132 may be configured to emit a magnetic field 133 in a first direction 135 and the magnetic field sensor 134 may be configured to face a second direction 136 to receive and detect the magnetic field 133, with the first direction 135 and the second direction 136 being opposite yet coaxial. In one embodiment, the ultrasonic elements 142, 144 utilize a similar coaxial signal alignment in order to obtain accurate and reliable structural information from the ultrasonic signal 143. For example, coaxial signal alignment may mean that the transmission direction of the ultrasonic signal 143 emitted from the ultrasonic transmit transducer 142 is perpendicular to the tangent of the external face-sheet 71 of the sandwich panel 70 and coaxial with a signal reception direction of the ultrasonic receive transducer 144, the signal reception direction also being perpendicular to the tangent of the internal face-sheet 72 of the sandwich panel 70. In one embodiment, the signal axis of the magnetic field is the symmetrical axis of the magnetic field that extends centrally through the magnetic field.

The described orientation of the probes 110, 120 prevents leakage of couplant gel. Additionally, the detection of structural characteristic data is based on the ultrasonic signal 143 transmitted and received from a properly oriented ultrasonic transmit transducer 142 and a properly oriented ultrasonic receive transducer 144 inspection probe. The described orientation of the probes 110, 120 ensures the ultrasonic signal 143 is consistent and accurate. In other words, if the probes are positioned so that the ultrasonic elements 142, 144 are not in coaxial signal alignment, the detected ultrasonic signal 143 may be skewed and any structural analysis based on the skewed data may be flawed.

Figure 1B:
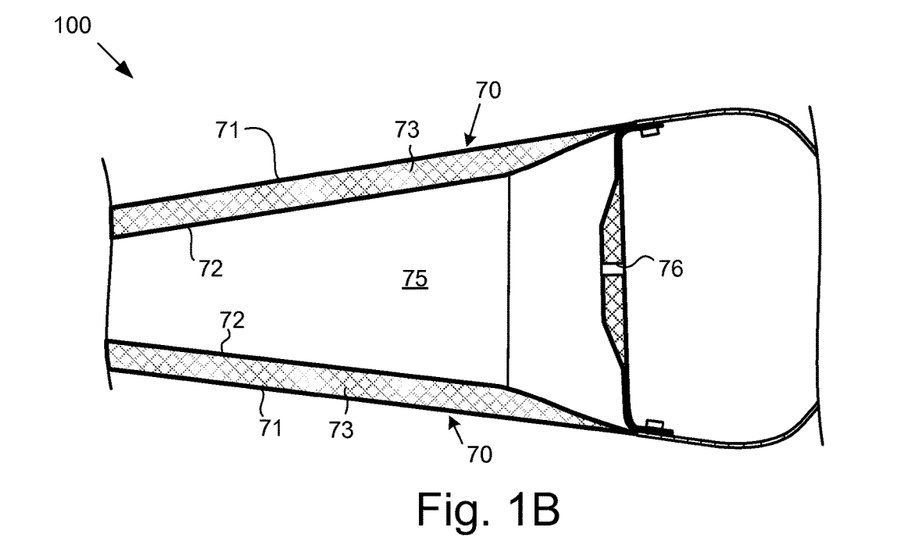
FIG. 1B is a cross-sectional side view of sandwich panels defining an enclosed space within a portion of an airframe, according to one embodiment.
Figure 1C:
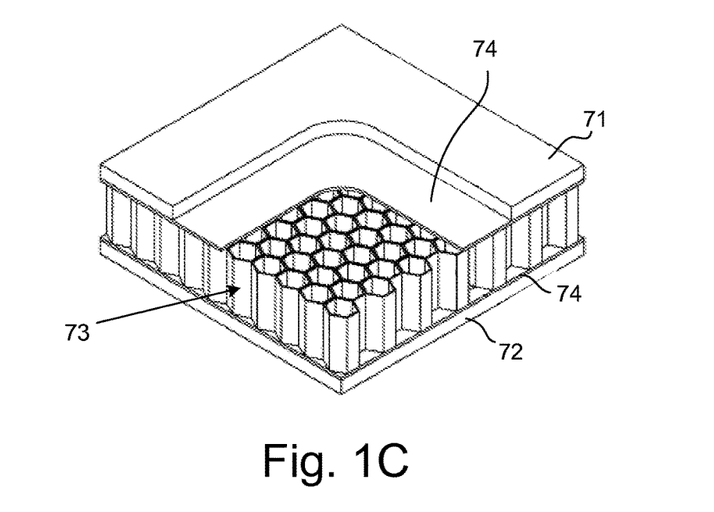
FIG. 1C is a partial cutout perspective view of a sandwich panel with a honeycomb core material, according to one embodiment.

FIG. 1B is a cross-sectional side view of sandwich panels 70 defining an enclosed space 75 within a portion of an airframe and FIG. 1C is a partial cutout perspective view of one embodiment of the sandwich panel 70 with a honeycomb core material 73. As mentioned above, the sandwich panel 70 may form part of an airframe or other structural assembly of an aircraft. Repairing a structural component of an airframe often involves heating certain elements in order to set and/or cure the repair. However, the heating required to cure the plastics or adhesives used during the repair often exceeds the boiling point of water, which may result in any moisture accumulated inside the panel 70 to vaporize, expand, and damage the honeycomb core 73. As a result, conventional repairs to honeycomb material include extensive drying practices to remove excess moisture from the panels 70. Accordingly, inspecting a sandwich panel 70 having a honeycomb core material 73 after a repair is important, not just to the region immediately surrounding the repair, but to any surrounding regions as well to ensure the honeycomb core material 73 has not been damaged by residual moisture.

In one embodiment, the enclosed space 75 may not be entirely surrounded by the sandwich panel 70 but may instead have one or more sides that are formed from a different material, such as the metal or composite spar 77 shown in FIG. 1A. In other words, in one embodiment the access hole 76 is in the sandwich panel 70 while in another embodiment the access hole 76 is in a different material, such as the spar 77.

The sandwich panel 70, shown in FIG. 1B, can be any of various components made from any of various materials. In some implementations, the sandwich panel 70 is made from an external face-sheet 71 and an internal face-sheet 72 with a core material 73 interposed between the face-sheets. In one embodiment, the core material 73 has a honeycomb structure. The face-sheets 71, 72 and core material 73 may be made from a metal, such as steel and aluminum. In other implementations, the face-sheets 71, 72 and core material 73 may be made from non-metallic materials, such as graphite, composite, ceramic, polymer, and the like. The face-sheets 71 and 72 may be bonded to the core material 73 in an autoclave or oven using a pre-positioned adhesive bond material 74.

Figure 2:
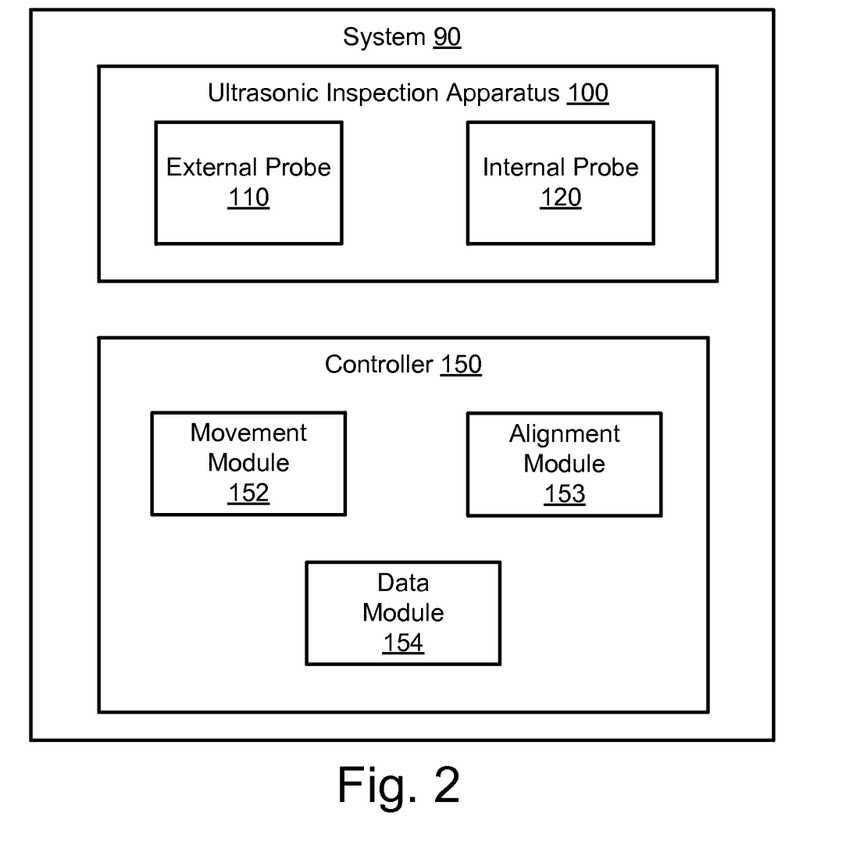
FIG. 2 is a schematic block diagram of one embodiment of a system for inspecting a sandwich panel defining an enclosed space.

FIG. 2 is a schematic block diagram of one embodiment of a system 90 for inspecting the sandwich panel 70 defining an enclosed space 75. The system 90 includes the apparatus 100 described above but also includes a controller 150 for automating the inspection process. In the depicted embodiment, the controller 150 includes a movement module 152, an alignment module 153, and a data module 154. The movement module 152 is configured to move one of the external probe 110 and the internal probe 120 to an inspection position. The alignment module 153 is configured to move the other of the external probe 110 and the internal probe 120 to an alignment position. The data module 154 is configured to detect the ultrasonic signal 143 from the ultrasonic transmit transducer by the ultrasonic receive transducer when the one of the external probe and the internal probe is in the inspection position and when the other of the external probe and the internal probe is in the alignment position. In other words, as described above, the probes 110, 120 may be moved across their respective face-sheets 71, 72 of the sandwich panel 70 and the magnetic elements 132, 134 can be used to align the probes 110, 120, thereby ensuring that the ultrasonic through-transmission inspection of the sandwich panel by the ultrasonic elements 142, 144 is accurate and consistent.

In one embodiment, the movement module 152 is configured to implement a movement pattern of one of the probes 110, 120 across the respective face-sheet 71, 72 of the sandwich panel 70. For example, the movement module 152 may include preprogrammed/predetermined movement patterns and associated robotic algorithms for actuating the movement pattern with robotic device, thus enabling the inspection procedure to step through multiple grid points of a plurality of grid points in order to comprehensively inspect the sandwich panel 70.

The alignment module 153, as described above, may be configured to move the probe not moved by the movement module 152. In other words, the alignment module communicates with the magnetic elements 132, 134 to properly align the probes in preparation for a reliable ultrasonic through-transmission. Generally, the movement module 152 moves the external probe 110 through a series of desired inspection locations and the alignment module 153, using the magnetic elements 132, 134, aligns the internal probe 120 with the external probe 110.

The controller 150 may be coupled to a robotic device. In one embodiment, the controller 150 may be integrated or coupled to a computer or a computer network that is electronically coupled to a robotic device. In a further embodiment, the controller 150 and its various modules 152, 153, 154 are implemented using various electronic devices. The robotic device may be a robotic arm that is rotatable, pivotable, and/or extendable in a variety of different manners in order to position the probes 110, 120 in a plurality of positions.

In one embodiment, the data module 154 is further configured to determine the presence of structural anomalies by comparing the received ultrasonic signal with the transmitted ultrasonic signal and/or by comparing the received ultrasonic signal 143 with an expected ultrasonic reading. In other words, the ultrasonic signal received by the ultrasonic receive transducer 144 may be compared with the transmitted ultrasonic signal from the ultrasonic transmit transducer and/or an expected ultrasonic reading from a control sandwich panel that is free from structural defects. If the compared difference is greater than a predetermined threshold, the data module 154 determines that a structural anomaly/defect is present in the sandwich panel 70. For example, the data module 154 may compare the amplitude/magnitude difference between the transmitted ultrasonic signal and the received ultrasonic signal and/or the expected ultrasonic reading. In one embodiment, for example, the data module 154 may determine that a structural anomaly is present if the difference between the received ultrasonic signal and the expected ultrasonic reading is more than 18 decibels. In another embodiment, the data module 154 may compare characteristics, other than magnitude, of the received ultrasonic signal, such as frequency content.

Figure 3:
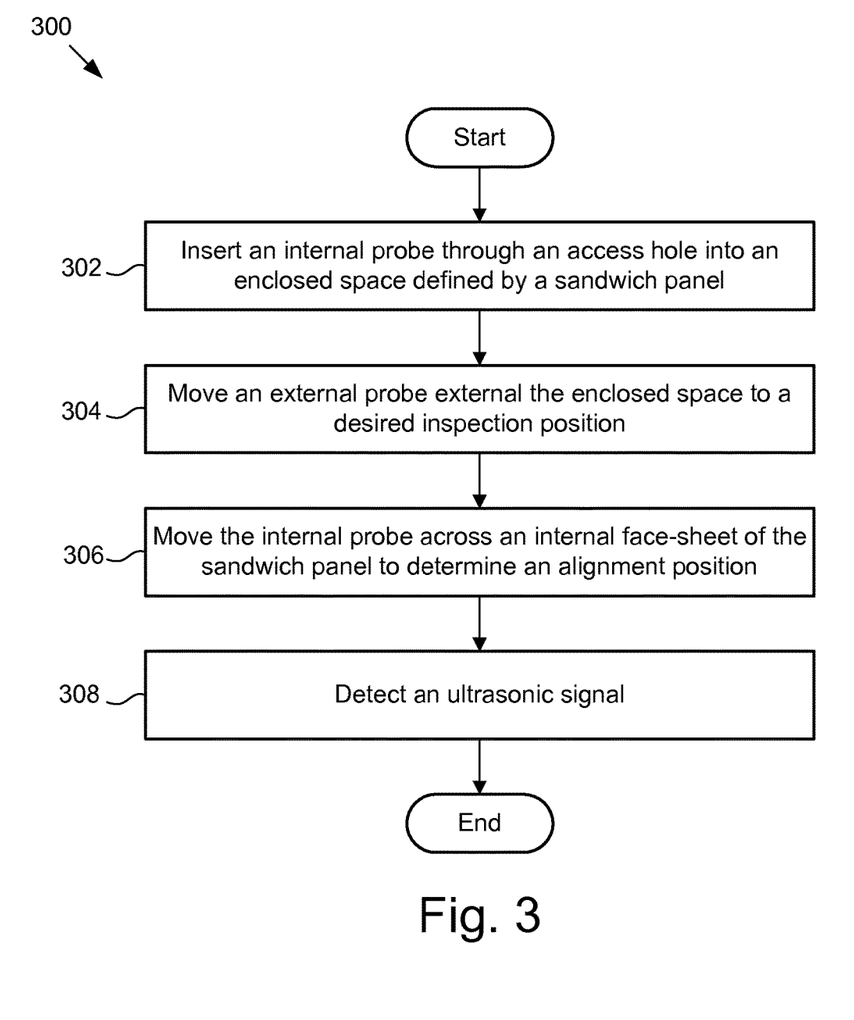
FIG. 3 is a schematic flowchart diagram of a method for inspecting a sandwich panel defining an enclosed space, according to one embodiment.

FIG. 3 is a schematic flowchart diagram of a method 300 for inspecting a sandwich panel 70 defining an enclosed space 75, according to one embodiment. The method 300 includes inserting an internal probe 120 through the access hole 76 at 302. At least a portion of the extension arm 122 remains external the enclosed space 75. The method 300 further includes moving the external probe 110 external the enclosed space 75 to a desired inspection position on the external face-sheet 71 of the sandwich panel 70 at 304. After moving the external probe 110 to the desired inspection position, the method 300 includes moving the internal probe 120 across the internal face-sheet 72 of the sandwich panel 70 at 306 to determine an alignment position where a maximum magnetic field strength of a magnetic field 133 emanating from the magnetic field emitter 132 of one of the internal and external probe is detected by the magnetic field sensor 134 of the other of the internal 120 and external probe 110. When the external probe 110 is at the desired inspection position and the internal probe 120 is at the alignment position, the method 300 includes detecting the ultrasonic signal from the ultrasonic transmit transducer 142 of one of the internal 120 and external probe 110 by the ultrasonic receive transducer 144 of the other of the internal 120 and external probe 110 at 308.

The method 300 may further include applying a couplant gel to the internal face-sheet 72 of the sandwich panel 70 before inserting the internal probe 120 through the access hole 76 so that moving the internal probe 120 across the internal face-sheet 72 of the sandwich panel 70 includes moving the ultrasonic receive transducer 144 across the internal face-sheet 72 of the sandwich panel in contact with the couplant gel. The method 300 may also include applying a couplant gel to the external face-sheet 71 of the sandwich panel 70 before moving the external probe 110 to the desired inspection point and contacting the ultrasonic transmit transducer 142 of the external probe 110 to with couplant gel.

In one embodiment, the couplant gel may be water, oil, propylene glycol, glycerin, gel, and the like, to facilitate and promote the transmission and propagation of the ultrasonic signal/waves.

In one implementation, detecting the ultrasonic signal from the ultrasonic transmit transducer by the ultrasonic receive transducer includes continually transmitting and receiving ultrasounds but only recording the ultrasonic signal when the external probe is at the desired inspection position and the internal probe is at the alignment position. In yet another implementation, detecting the ultrasonic signal from the ultrasonic transmit transducer by the ultrasonic receive transducer comprises transmitting and receiving ultrasounds only when the external probe is at the desired inspection position and the internal probe is at the alignment position.

Figure 4:
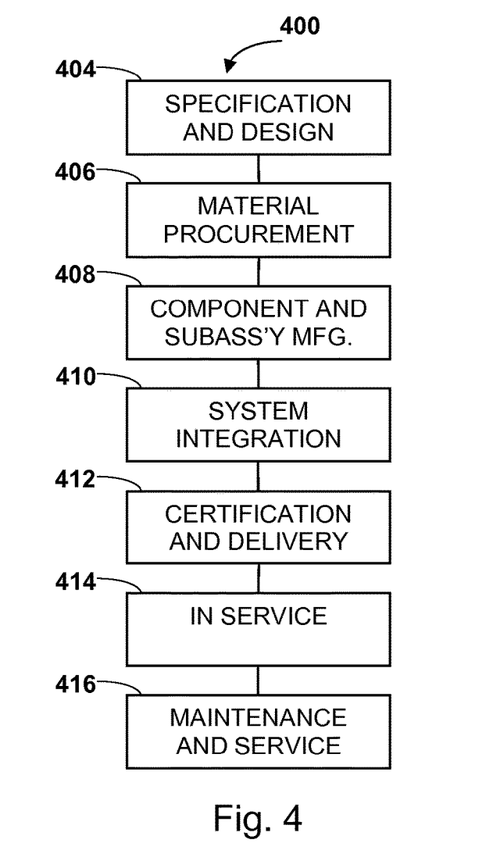
FIG. 4 is a schematic flowchart diagram of an aircraft production and service methodology, according to one embodiment.
Figure 5:
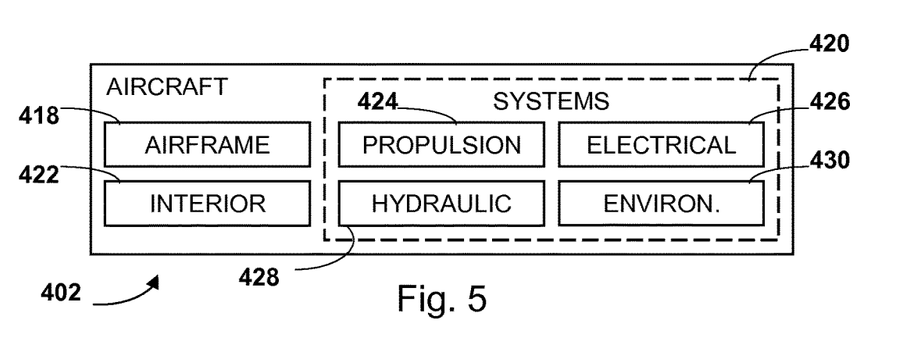
FIG. 5 is a schematic block diagram of an aircraft, according to one embodiment.

Referring more particularly to the drawings, embodiments of the disclosure may be described in the context of an aircraft manufacturing and service method 400 as shown in FIG. 4 and an aircraft 402 as shown in FIG. 5. During pre-production, exemplary method 400 may include specification and design 404 of the aircraft 402 and material procurement 406. During production, component and subassembly manufacturing 408 and system integration 410 of the aircraft 402 takes place. Thereafter, the aircraft 402 may go through certification and delivery 412 in order to be placed in service 414. While in service by a customer, the aircraft 402 is scheduled for routine maintenance and service 416 (which may also include modification, reconfiguration, refurbishment, and so on).

Each of the processes of method 400 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 5, the aircraft 402 produced by exemplary method 400 may include an airframe 418 with a plurality of systems 420 and an interior 422. Examples of high-level systems 420 include one or more of a propulsion system 424, an electrical system 426, a hydraulic system 426, and an environmental system 430. Any number of other systems may be included. Although an aerospace example is shown, the principles of the invention may be applied to other industries, such as the automotive industry.

Apparatus and methods embodied herein may be employed during any one or more of the stages of the production and service method 400. For example, components or subassemblies corresponding to production process 408 may be fabricated or manufactured in a manner similar to components or subassemblies produced while the aircraft 402 is in service. Also, one or more apparatus embodiments, method embodiments, or a combination thereof may be utilized during the production stages 408 and 410, for example, by substantially expediting assembly of or reducing the cost of an aircraft 402. Similarly, one or more of apparatus embodiments, method embodiments, or a combination thereof may be utilized to detect structural defects while the aircraft 402 is in service, for example and without limitation, to maintenance and service 416.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing.

In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages (e.g., LabVIEW). The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. An apparatus for non-destructively inspecting a sandwich panel defining an enclosed space, the apparatus comprising:
    an external probe adjacent an external face-sheet of the sandwich panel, the external probe comprising and integrally formed from:
        one of a magnetic field emitter or a magnetic field sensor, the magnetic field emitter emitting a magnetic field and the magnetic field sensor detecting a magnetic field strength of the magnetic field; and
        one of an ultrasonic transmit transducer or an ultrasonic receive transducer; and
    an internal probe adjacent an internal face-sheet of the sandwich panel, the sandwich panel comprising a core material interposed between the external and internal face-sheets, the internal probe comprising and integrally formed from:
        the other of the magnetic field emitter or the magnetic field sensor; and
        the other of the ultrasonic transmit transducer or the ultrasonic receive transducer.

2. The apparatus of claim 1, wherein non-destructive access to the enclosed space is limited to an access hole having a diameter less than 3 inches.

3. The apparatus of claim 2, wherein the internal probe has a cross-sectional dimension that is less than the diameter of the access hole such that the internal probe is passable through the access hole.

4. The apparatus of claim 1, wherein the internal probe is affixed to an extension arm, wherein the extension arm is positionable to extend from an access hole to allow a user to grasp a portion of the extension arm external the enclosed space and control the position of the internal probe within the enclosed space.

5. The apparatus of claim 1, wherein the core material of the sandwich panel has a honeycomb structure.

6. The apparatus of claim 1, wherein the external probe comprises the magnetic field sensor and the ultrasonic transmit transducer, wherein the magnetic field sensor comprises an eddy current sensor coil wrapped around and concentric with the ultrasonic transmit transducer.

7. The apparatus of claim 6, wherein the internal probe comprises the magnetic field emitter and the ultrasonic receive transducer, wherein the magnetic field emitter comprises multiple magnetic material components circumferentially positioned around and collectively concentric with the ultrasonic receive transducer.

8. The apparatus of claim 1, wherein the magnetic field emitter is a material having a relative magnetic permeability between about 16 and about 5,000 and the magnetic field sensor is an eddy current sensor coil.

9. A method for non-destructively inspecting a sandwich panel defining an enclosed space, the method comprising:
   inserting an internal probe through an access hole to the enclosed space, wherein the internal probe is affixed to an extension arm and at least a portion of the extension arm remains external the enclosed space;
   moving an external probe external the enclosed space to a desired inspection position on an external face-sheet of the sandwich panel;
   after moving the external probe to the desired inspection position, moving the internal probe across an internal face-sheet of the sandwich panel to determine an alignment position where a maximum magnetic field strength of a magnetic field emanating from a magnetic field emitter of one of the internal or external probe is detected by a magnetic field sensor of the other of the internal or external probe; and
   when the external probe is at the desired inspection position and the internal probe is at the alignment position, detecting an ultrasonic signal from an ultrasonic transmit transducer of one of the internal or external probe by an ultrasonic receive transducer of the other of the internal or external probe.

10. The method of claim 9, further comprising applying a couplant gel to the internal face-sheet of the sandwich panel before inserting the internal probe through the access hole, wherein moving the internal probe across the internal face-sheet of the sandwich panel comprises moving the ultrasonic receive transducer across the internal face-sheet of the sandwich panel in contact with the couplant gel.

11. The method of claim 9, further comprising applying a couplant gel to the external face-sheet of the sandwich panel before moving the external probe to the desired inspection position and contacting the ultrasonic transmit transducer of the external probe to the external face-sheet of the sandwich panel via couplant gel.

12. The method of claim 9, further comprising determining a presence of structural anomalies by comparing the ultrasonic signal with an expected ultrasonic reading.

13. The method of claim 12, wherein a structural anomaly is present if a difference between the ultrasonic signal and the expected ultrasonic reading is more than 18 decibels.

14. The method of claim 9, wherein moving the external probe is automated by a robotic device controlled by a controller.

15. The method of claim 9, wherein moving the internal probe is automated by a robotic device controlled by a controller.

16. The method of claim 9, wherein detecting the ultrasonic signal from the ultrasonic transmit transducer by the ultrasonic receive transducer comprises continually transmitting and receiving ultrasounds but only recording the ultrasonic signal when the external probe is at the desired inspection position and the internal probe is at the alignment position.

17. The method of claim 9, wherein detecting the ultrasonic signal from the ultrasonic transmit transducer by the ultrasonic receive transducer comprises transmitting and receiving ultrasounds only when the external probe is at the desired inspection position and the internal probe is at the alignment position.

18. An inspection system for non-destructively inspecting a sandwich panel defining an enclosed space, the system comprising:
   an external probe adjacent an external face-sheet of the sandwich panel, the external probe comprising and integrally formed from:
      one of a magnetic field emitter or a magnetic field sensor, the magnetic field emitter emitting a magnetic field; and
      one of an ultrasonic transmit transducer or an ultrasonic receive transducer; and
   an internal probe adjacent an internal face-sheet of the sandwich panel, the sandwich panel comprising a core material interposed between the external and internal face-sheets, the internal probe comprising and integrally formed from:
      the other of the magnetic field emitter or the magnetic field sensor; and
      the other of the ultrasonic transmit transducer or the ultrasonic receive transducer
   a controller comprising:
      a movement module configured to move one of the external probe and the internal probe to an inspection position;
      an alignment module configured to move the other of the external probe and the internal probe to an alignment position; and
      a data module configured to detect an ultrasonic signal from the ultrasonic transmit transducer by the ultrasonic receive transducer when the one of the external probe or the internal probe is in the inspection position and when the other of the external probe or the internal probe is in the alignment position.

19. The system of claim 18, wherein the data module is further configured to determine a presence of structural anomalies by comparing the ultrasonic signal with an expected ultrasonic reading.

20. The system of claim 19, wherein a structural anomaly is present if a difference between the ultrasonic signal and the expected ultrasonic reading is more than 18 decibels.

* * * * *